US008057475B2

(12) United States Patent
Michelson

(10) Patent No.: US 8,057,475 B2
(45) Date of Patent: Nov. 15, 2011

(54) THREADED INTERBODY SPINAL FUSION IMPLANT

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/942,671

(22) Filed: Nov. 9, 2010

(65) Prior Publication Data

US 2011/0054529 A1    Mar. 3, 2011

Related U.S. Application Data

(63) Continuation of application No. 12/454,393, filed on May 18, 2009, now Pat. No. 7,828,800, which is a continuation of application No. 08/480,908, filed on Jun. 7, 1995, now Pat. No. 7,534,254.

(51) Int. Cl.
    A61F 17/56     (2006.01)
(52) U.S. Cl. .......................................... 606/60; 606/246
(58) Field of Classification Search .................... 606/53, 606/240, 246, 60; 623/17.1, 17.3
    See application file for complete search history.

(56) References Cited

U.S. PATENT DOCUMENTS

| 350,420 A | 10/1886 | Dillon |
| 1,137,585 A | 4/1915 | Craig |
| 2,065,659 A | 12/1936 | Cullen |
| 2,181,746 A | 11/1939 | Siebrandt |
| 2,243,718 A | 5/1941 | Moreira |
| 2,372,622 A | 3/1945 | Fassio |
| 2,514,665 A | 7/1950 | Myller |
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |
| 2,842,131 A | 7/1958 | Smith |
| 2,878,809 A | 3/1959 | Treace |
| 3,128,768 A | 4/1964 | Geistauts |
| 3,298,372 A | 1/1967 | Feinberg |
| 3,426,364 A | 2/1969 | Lumb |
| 3,486,505 A | 12/1969 | Morrison |

(Continued)

FOREIGN PATENT DOCUMENTS

DE    1 961 531    7/1970

(Continued)

OTHER PUBLICATIONS

Adams, et al.; Outline of Orthopaedics, Eleventh Edition; Trunk and Spine, p. 194.

(Continued)

*Primary Examiner* — Michael A. Brown
(74) *Attorney, Agent, or Firm* — Martin & Ferraro, LLP

(57) ABSTRACT

The present invention is directed to a variety of interbody spinal fusion implants having at least a partially frusto-conical configuration. An external thread is employed to increase implant stability and implant surface area, and for the purpose of advancing the spinal fusion implant into the fusion site. The spinal fusion implants of the present invention may be relatively solid or hollow and may have surface roughenings to promote bone ingrowth and stability. The spinal fusion implants of the present invention may have wells extending into the material of the implant from the surface for the purpose of holding fusion promoting materials and to provide for areas of bone ingrowth fixation.

28 Claims, 4 Drawing Sheets

U.S. PATENT DOCUMENTS

| | | | |
|---|---|---|---|
| 3,604,487 A | 9/1971 | Gilbert | |
| 3,605,123 A | 9/1971 | Hahn | |
| 3,618,611 A | 11/1971 | Urban | |
| 3,709,219 A | 1/1973 | Halloran | |
| 3,719,186 A | 3/1973 | Merig, Jr. | |
| 3,720,959 A | 3/1973 | Hahn | |
| 3,750,652 A | 8/1973 | Sherwin | |
| 3,848,001 A | 11/1974 | Ma et al. | |
| 3,855,638 A | 12/1974 | Pilliar | |
| 3,866,510 A | 2/1975 | Eibes et al. | |
| 3,867,728 A | 2/1975 | Stubstad et al. | |
| 3,867,950 A | 2/1975 | Fischell | |
| 3,875,595 A | 4/1975 | Froning | |
| 3,888,260 A | 6/1975 | Fischell | |
| 3,892,232 A | 7/1975 | Neufeld | |
| 3,905,047 A | 9/1975 | Long | |
| 3,915,151 A | 10/1975 | Kraus | |
| 3,916,907 A | 11/1975 | Peterson | |
| 3,918,440 A | 11/1975 | Kraus | |
| 3,942,535 A | 3/1976 | Schulman | |
| 3,948,262 A | 4/1976 | Zaffaroni | |
| 3,952,334 A | 4/1976 | Bokros et al. | |
| 3,987,499 A | 10/1976 | Scharbach et al. | |
| 4,003,287 A | 1/1977 | Ziaylek, Jr. | |
| 4,016,651 A | 4/1977 | Kawahara et al. | |
| 4,027,392 A | 6/1977 | Sawyer et al. | |
| D245,259 S | 8/1977 | Shen | |
| 4,051,905 A | 10/1977 | Kleine | |
| 4,059,115 A | 11/1977 | Jumashev et al. | |
| 4,070,514 A | 1/1978 | Eatherly et al. | |
| 4,082,097 A | 4/1978 | Mann et al. | |
| 4,086,701 A | 5/1978 | Kawahara et al. | |
| 4,124,026 A | 11/1978 | Berner et al. | |
| 4,142,517 A | 3/1979 | Stavropoulos et al. | |
| 4,168,326 A | 9/1979 | Broemer et al. | |
| 4,175,555 A | 11/1979 | Herbert | |
| 4,177,524 A | 12/1979 | Grell et al. | |
| 4,181,457 A | 1/1980 | Holmes | |
| 4,197,850 A | 4/1980 | Schulman et al. | |
| 4,206,516 A | 6/1980 | Pilliar | |
| 4,222,128 A | 9/1980 | Tomonaga et al. | |
| D257,511 S | 11/1980 | Zahn | |
| 4,232,679 A | 11/1980 | Schulman | |
| 4,237,948 A | 12/1980 | Jones et al. | |
| 4,258,716 A | 3/1981 | Sutherland | |
| 4,259,072 A | 3/1981 | Hirabayashi et al. | |
| 4,262,369 A | 4/1981 | Roux | |
| 4,271,832 A | 6/1981 | Evans et al. | |
| D260,525 S | 9/1981 | Lassiter | |
| 4,289,123 A | 9/1981 | Dunn | |
| 4,293,962 A | 10/1981 | Fuson | |
| 4,309,777 A | 1/1982 | Patil | |
| 4,328,593 A * | 5/1982 | Sutter et al. | 623/23.42 |
| 4,333,469 A | 6/1982 | Jeffcoat et al. | |
| 4,341,206 A | 7/1982 | Perrett et al. | |
| 4,349,921 A | 9/1982 | Kuntz | |
| 4,356,572 A | 11/1982 | Guillemin et al. | |
| 4,401,112 A | 8/1983 | Rezaian | |
| 4,405,319 A | 9/1983 | Cosentino | |
| 4,414,979 A | 11/1983 | Hirshorn et al. | |
| 4,423,721 A | 1/1984 | Otte et al. | |
| 4,439,152 A | 3/1984 | Small | |
| 4,450,834 A | 5/1984 | Fischer | |
| 4,484,570 A | 11/1984 | Sutter et al. | |
| 4,492,226 A | 1/1985 | Belykh et al. | |
| 4,497,320 A | 2/1985 | Nicholson et al. | |
| 4,501,269 A * | 2/1985 | Bagby | 606/279 |
| 4,507,115 A | 3/1985 | Kambara et al. | |
| RE31,865 E | 4/1985 | Roux | |
| 4,530,360 A | 7/1985 | Duarte | |
| 4,535,374 A | 8/1985 | Anderson et al. | |
| 4,535,485 A | 8/1985 | Ashman et al. | |
| 4,542,539 A | 9/1985 | Rowe, Jr. et al. | |
| 4,545,374 A | 10/1985 | Jacobson | |
| 4,547,390 A | 10/1985 | Ashman et al. | |
| 4,549,547 A | 10/1985 | Brighton et al. | |
| 4,552,200 A | 11/1985 | Sinha et al. | |
| 4,553,273 A | 11/1985 | Wu | |
| 4,554,914 A | 11/1985 | Kapp et al. | |
| D281,814 S | 12/1985 | Pratt et al. | |
| 4,570,623 A | 2/1986 | Ellison et al. | |
| 4,570,624 A | 2/1986 | Wu | |
| 4,592,346 A | 6/1986 | Jurgutis | |
| 4,599,086 A | 7/1986 | Doty | |
| 4,600,000 A | 7/1986 | Edwards | |
| 4,602,638 A | 7/1986 | Adams | |
| 4,604,995 A | 8/1986 | Stephens | |
| 4,608,052 A | 8/1986 | Van Kampen et al. | |
| 4,611,581 A | 9/1986 | Steffee | |
| 4,619,264 A | 10/1986 | Singh | |
| 4,628,921 A | 12/1986 | Rousso | |
| 4,634,720 A | 1/1987 | Dorman et al. | |
| 4,636,217 A | 1/1987 | Ogilvie et al. | |
| 4,636,526 A | 1/1987 | Dorman et al. | |
| 4,645,503 A | 2/1987 | Lin et al. | |
| 4,653,486 A | 3/1987 | Coker | |
| 4,655,777 A | 4/1987 | Dunn | |
| 4,661,536 A | 4/1987 | Dorman et al. | |
| 4,664,567 A | 5/1987 | Edwards | |
| 4,665,920 A | 5/1987 | Campbell | |
| 4,677,883 A | 7/1987 | Lee | |
| 4,677,972 A | 7/1987 | Tornier | |
| 4,693,721 A | 9/1987 | Ducheyne | |
| 4,696,290 A | 9/1987 | Steffee | |
| 4,698,375 A | 10/1987 | Dorman et al. | |
| 4,710,075 A | 12/1987 | Davison | |
| 4,713,004 A | 12/1987 | Linkow et al. | |
| 4,714,469 A | 12/1987 | Kenna | |
| 4,721,103 A | 1/1988 | Freedland | |
| 4,736,738 A | 4/1988 | Lipovsek et al. | |
| 4,743,256 A | 5/1988 | Brantigan | |
| 4,743,260 A | 5/1988 | Burton | |
| 4,759,766 A | 7/1988 | Buettner-Janz et al. | |
| 4,759,769 A | 7/1988 | Hedman et al. | |
| 4,769,881 A | 9/1988 | Pedigo et al. | |
| 4,781,591 A | 11/1988 | Allen | |
| 4,790,303 A | 12/1988 | Steffee | |
| 4,805,602 A | 2/1989 | Puno et al. | |
| 4,820,305 A | 4/1989 | Harms et al. | |
| 4,830,000 A | 5/1989 | Shutt | |
| 4,834,757 A | 5/1989 | Brantigan | |
| 4,848,327 A | 7/1989 | Perdue | |
| 4,851,008 A | 7/1989 | Johnson | |
| 4,863,476 A | 9/1989 | Shepperd | |
| 4,863,477 A | 9/1989 | Monson | |
| 4,865,603 A | 9/1989 | Noiles | |
| 4,877,020 A | 10/1989 | Vich | |
| 4,878,915 A | 11/1989 | Brantigan | |
| 4,903,882 A | 2/1990 | Long | |
| 4,904,260 A | 2/1990 | Ray et al. | |
| 4,904,261 A | 2/1990 | Dove et al. | |
| 4,911,718 A | 3/1990 | Lee et al. | |
| 4,913,144 A | 4/1990 | Del Medico | |
| 4,936,848 A | 6/1990 | Bagby | |
| 4,943,291 A | 7/1990 | Tanguy | |
| 4,955,885 A | 9/1990 | Meyers | |
| 4,955,908 A | 9/1990 | Frey et al. | |
| 4,957,495 A | 9/1990 | Kluger | |
| 4,960,420 A | 10/1990 | Goble et al. | |
| 4,961,740 A | 10/1990 | Ray et al. | |
| 4,968,316 A | 11/1990 | Hergenroeder | |
| 4,969,888 A | 11/1990 | Scholten et al. | |
| 4,987,904 A | 1/1991 | Wilson | |
| 5,015,247 A | 5/1991 | Michelson | |
| 5,015,255 A | 5/1991 | Kuslich | |
| 5,026,373 A * | 6/1991 | Ray et al. | 606/86 A |
| 5,030,236 A | 7/1991 | Dean | |
| 5,055,104 A | 10/1991 | Ray | |
| 5,059,193 A | 10/1991 | Kuslich | |
| 5,062,845 A | 11/1991 | Kuslich et al. | |
| 5,071,437 A | 12/1991 | Steffee | |
| 5,084,050 A | 1/1992 | Draenert | |
| 5,102,414 A | 4/1992 | Kirsch | |
| 5,108,422 A | 4/1992 | Green et al. | |
| 5,112,336 A | 5/1992 | Krevolin et al. | |
| 5,116,304 A | 5/1992 | Cadwell | |
| 5,122,130 A | 6/1992 | Keller | |

| | | | |
|---|---|---|---|
| 5,123,926 A | 6/1992 | Pisharodi | |
| 5,133,755 A | 7/1992 | Brekke | |
| 5,171,278 A | 12/1992 | Pisharodi | |
| 5,192,327 A | 3/1993 | Brantigan | |
| 5,246,458 A | 9/1993 | Graham | |
| 5,258,031 A | 11/1993 | Salib et al. | |
| 5,263,953 A | 11/1993 | Bagby | |
| 5,279,292 A | 1/1994 | Baumann et al. | |
| 5,282,861 A | 2/1994 | Kaplan | |
| 5,292,252 A | 3/1994 | Nickerson et al. | |
| 5,306,309 A | 4/1994 | Wagner et al. | |
| 5,314,427 A | 5/1994 | Goble et al. | |
| 5,324,295 A | 6/1994 | Shapiro | |
| 5,352,229 A | 10/1994 | Goble et al. | |
| 5,360,430 A | 11/1994 | Lin | |
| 5,364,399 A | 11/1994 | Lowery et al. | |
| 5,370,662 A | 12/1994 | Stone et al. | |
| 5,370,697 A | 12/1994 | Baumgartner | |
| 5,393,036 A | 2/1995 | Sheridan | |
| RE34,871 E | 3/1995 | McGuire et al. | |
| 5,396,880 A | 3/1995 | Kagan et al. | |
| 5,397,359 A | 3/1995 | Mittelmeier et al. | |
| 5,397,364 A | 3/1995 | Kozak et al. | |
| 5,425,772 A | 6/1995 | Brantigan | |
| 5,435,723 A | 7/1995 | O'Brien | |
| 5,443,514 A | 8/1995 | Steffee | |
| 5,458,638 A | 10/1995 | Kuslich et al. | |
| 5,489,307 A * | 2/1996 | Kuslich et al. | 128/898 |
| 5,489,308 A | 2/1996 | Kuslich et al. | |
| 5,571,109 A | 11/1996 | Bertagnoli | |
| 5,571,189 A | 11/1996 | Kuslich | |
| 5,669,909 A | 9/1997 | Zdeblick et al. | |
| 5,683,463 A | 11/1997 | Godefroy et al. | |
| 5,766,252 A | 6/1998 | Henry et al. | |
| 5,782,919 A | 7/1998 | Zdeblick et al. | |
| D397,439 S | 8/1998 | Koros et al. | |
| 5,800,547 A | 9/1998 | Schafer et al. | |
| 5,906,616 A | 5/1999 | Pavlov et al. | |
| 6,118,043 A | 9/2000 | Nies et al. | |
| 7,534,254 B1 | 5/2009 | Michelson | |
| 7,828,800 B2 | 11/2010 | Michelson | |
| 2002/0138144 A1 | 9/2002 | Michelson | |

FOREIGN PATENT DOCUMENTS

| | | |
|---|---|---|
| DE | 24 46 039 | 4/1975 |
| DE | 29 10 627 | 9/1980 |
| DE | 31 01 333 A1 | 12/1981 |
| DE | 31 32 520 A1 | 6/1982 |
| DE | 35 05 567 A1 | 6/1986 |
| DE | 36 08 163 A1 | 9/1987 |
| DE | 41 04 359 A1 | 8/1992 |
| DE | 43 02 397 A1 | 7/1993 |
| EP | 0 077 159 | 4/1983 |
| EP | 0 162 005 | 11/1985 |
| EP | 0 179 695 | 4/1986 |
| EP | 0 260 044 | 3/1988 |
| EP | 0 303 241 A2 | 2/1989 |
| EP | 0 307 241 | 3/1989 |
| EP | 0 499 465 A1 | 8/1992 |
| EP | 0 551 187 A1 | 7/1993 |
| EP | 0 577 179 A1 | 1/1994 |
| EP | 0 599 419 A2 | 6/1994 |
| EP | 0 732 093 A2 | 9/1996 |
| ES | 283078 | 5/1985 |
| FR | 2 295 729 | 7/1976 |
| FR | 2 581 336 | 11/1986 |
| FR | 2 703 580 | 10/1994 |
| GB | 1 291 470 | 10/1972 |
| GB | 1 492 990 | 11/1977 |
| GB | 1 531 487 | 11/1978 |
| GB | 2 076 657 A | 12/1981 |
| GB | 2 083 754 | 3/1982 |
| GB | 2 126 094 A | 3/1984 |
| GB | 2 164 277 A | 3/1986 |
| JP | 57-29348 | 2/1982 |
| JP | 60-31706 | 2/1985 |
| JP | 60-43984 | 3/1985 |
| JP | 61-122859 | 6/1986 |
| JP | 62-155846 | 7/1987 |
| SE | 106 101 | 7/1939 |
| SU | 1107854 | 8/1984 |
| SU | 1124960 | 11/1984 |
| SU | 1217374 | 3/1986 |
| SU | 1222254 | 4/1986 |
| WO | WO 84/01298 | 4/1984 |
| WO | WO 91/06266 | 5/1991 |
| WO | WO 92/14423 | 9/1992 |
| WO | WO 93/01771 | 2/1993 |

OTHER PUBLICATIONS

Herkowitz, et al.; Principles of Bone Fusion; The Spine, Third Edition; Chapter 44, p. 1739.

Muschler, et al.; The Biology of Spinal Fusion; Spinal Fusion Science and Technique, Cotler and Cotler, pp. 9-13.

Zindrick, et al.; Lumbar Spine Fusion: Different Types and Indications; The Lumbar Spine, vol. 1, Second Edition, pp. 588-593 (1996).

Gillingham, F.J.; Automatic Patient Monitoring in the Ward; Brit. Surg , vol. 53, No. 10, pp. 864-866 (Oct. 1966).

Maloney, A.F.J., et al.; Clinical and Pathological Observations in Fatal Head Injuries Brit. J. Surg., vol. 56, No. 1, pp. 23-31 (Jan. 1969).

Harris, P., et al., Spinal Deformity After Spinal Cord Injury, Paraplegia, vol. 6, No. 4, pp. 232-238 (Feb. 1969).

Gillingham, F.J., et al.; Head injuries; Proceedings of the 18th World Congress of the International College of Surgeons, Rome, pp. 68-71 (May 28-31, 1972).

Whatmore, W. J.; Sincipitai Encephalomeningoceles; Brit. J. Sung., vol. 60, No. 4, pp. 261-270 (Apr. 1973).

Whatmore, W. J.; Meningioma Following Trauma; Brit, J. Surg., vol. 60, No. 6, pp. 496-498 (Jun. 1973).

Bagby, George W.; Wobbler Syndrome n. Horses (the Ataxic Horse); Spokane County Medical Society Bulletin; Spring 1979.

Rathke, F.W., et al.; Surgery of the Spine; Atlas of Orthopaedic Operations, vol. 1, p. 137, W.B. Saunders Co., Philadelphia (1979).

Albrektsson, T., et al.; Osseointegrated Titanium implants; Acta. Orthop. Scand.; vol. 52:155-170 (1981).

Raveh, J., et al.; Neue Rekonstruktionsmoglichkeiten des Unterkiefers bei knochernen Defekten nach Turnorresektionen; Der Chirurg vol. 53:459-467 (1982).

Crock, H. V.; Practice of Spinal Surgery; Springer-Verlag/Wien, New York (1983).

DeBowes, R.M, et al.; Study of Bovine . . . Steel Baskets; Transactions of the 29th Annual Meeting; Orthopaedic Research Society, vol. 8, p. 407, Mar. 8-10 (1983).

O'Neill; P., et al.; Spinal Meningoceles in Association with Neurofibromatosis; Neurosurgery, vol, 13, No. 1, pp. 82-84 (Jul. 1983).

Brandt, L., et al.; A Dowel Inserter for Anterior Cervical interbody Fusion; J. Neurosurg. 61793-794 (Oct. 1984).

Whatmore, W.J., et al.; The Coventry Cervical Spreader and Dowel Inserter; ACTA Neurochirurgica, vol. 70, FASC. 1-2 (1984).

Raveh, J., et al.; Use of the Titanium-coated Hollow Screw and Reconstruction Plate System in Bridging of Lower Jaw Defects; J. Oral Maxtilofac Surg. 42:281-294 (1984).

Otero-Vich, Jose M.; Anterior Cervical Interbody Fusion with Threaded Cylindrical Bone; J. Neurosurg 63:750-753 (Nov. 1985).

Morscher, E., et al.; Die vordere Verplattung der Halswirbeisäule mit dem Hohlschrauben-Plattensystem aus Titanium, Der Chirurg, vol. 57, pp. 702-707 (1986) with English Translation.

Bagby, G.W.; Basket Implant Facilitates Spinal Fusion; Orthopedics Today, vol. 7, No. 10, (Oct. 1987).

Butts, M. K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse: Veterinary Surgery, vol. 17, No. 3, pp. 117-127 (1988).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).

Whatmore, W. J.; Proceedings of the Society of British Neurological Surgeons; Journal of Neurology, Neurosurgery, and Psychiatry, 50:1093-1100(1987).

Goldthwaite, N., et al.; Toward Percutaneous Spine Fusion; Ch. 45; Lumbar Spine Surgery; C.V. Mosby Company, pp. 512-522 (1987).

Bagby, G.W.; Arthrodesis by the Distraction-Compression Method Using a Stainless Steel Implant; Orthopedics, vol. II, No. 6, pp. 931-934 (Jun. 1987).

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).

The SpF-T Spinal Fusion Stimulator: An Efficacious Adjunct that Meets the Diverse Needs of Spine Patients; EBI Medical Systems; (Aug. 1991).

Schmitz at al.; Performance of Alloplastic Materials and Design of an Artificial Disc: The Artificial Disc; Brock, Mayer, Weigel; pp. 23-34 (1991).

The Use of Direct Current for Electrically Induced Osteogenesis; The Positive Effect of an Electronegative charge on Bone Growth; EBI Medical Systems (Feb. 1993).

Mylonas, C., et al.; Anterior Cervical Decompression and Fusion Using the Coventry Cervical Spreader and Dowel Inserter; British Journal of Neurosurgery, 7:545-549 (1993).

Fusion of the Lumbar Spine; Anterior Monosegmental Fusion L5-S1, Atlas of Spinal Operations, Thieme, pp. 270-274 (1993).

Spine Basics, Danek Group, Inc., Glossary (1993).

Lumbar Spine Surgery, Techniques & Complications; History of Lumbar Spine Surgery (1994) pp. 11-15; 27; 30; 35-45; 265-268.

European Search Report dated Aug. 4, 1999.

Cloward, Ralph B.; Sugical Techniques for Lumbar Disc Lesions; Codman; Signature Series 3.

Cloward, Ralph B.; Ruptured Cervical Intervertebral Discs: Removal of Disc & Osteophytes & Anterior Cervical Interbody Fusion (A.C.I.F.); Codman; Signature Series 4.

Cloward, Ralph B.; Recent Advances in Surgery of the Cervical Spine; pp, 285-293; German Society for Neurosurgery: vol. 2 Cervical Spine Operations; Excerpta Medica.

Hutter, Charles George; Spinal Stenosis and Posterior Lumbar interbody Fusion; pp. 103-114; Clinical Orthopaedics and Related Research; No. 193; The Association of Bone and Joint Surgeons.

Lin, Paul M.; Posterior Lumbar Interbody Fusion; pp. 114-122; Charles C. Thomas; Springfield, Illinois.

Lin, Paul M.; Lumbar Interbody Fusion: Principies and Techniques in Spine Surgery; Techniques and Complications: pp. 81, 98, 120, 146, 173, 180-184, 204, 224, 225, 231; Aspen Publishers, Inc.; 1989.

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Muller, M.E., Manual of Internal Fixation: Techniques Recommended by the AO Group; Second Edition, Expanded and Revised; pp. 3-20, 27-41, 53-58, 71-78, 94, 311, 320, Springer-Verlag, 1979.

Hierholzer, G.; Manual on the AO/ASIF Tubular External Fixator; pp. 85-91; Springer-Verlag; 1985.

Heim, Urs; Small Fragment Set Manual: Technique Recommended by the ASIF-Group; pp. 5-7, 10, 20, 21, 30; Springer-Verlag. 1974.

Harmon, Paul H.; Anterior Excision and Vertebral Body Fusion Operation for Intervertebral Disk Syndromes of the Lower Lumbar Spine: Three- to Five-Year Results in 244 Cases; pp. 107-127; Clinical Orthopaedics and Related Research, No, 26, J B. Lippincott.

Harmon, Paul H., A Simplified Surgical Technic for Anterior Lumbar Diskectomy and Fusion; Avoidance of Complications; Anatomy of the Retroperitoneal Veins; pp. 130-143; Clinical Orthopaedics and Related Research, No. 37, J.B. Lippincott Company, 1964.

Bullough, Peter G.; Atlas of Spinal Diseases; Figure 5.7; J,B, Lippencott Company; 1988.

Canale, S. Terry; Campbell's Operative Orthopaedics; vol. 3, 9th Edition; pp. 2191, 2216, 2459; Mosby, 1998.

\* cited by examiner

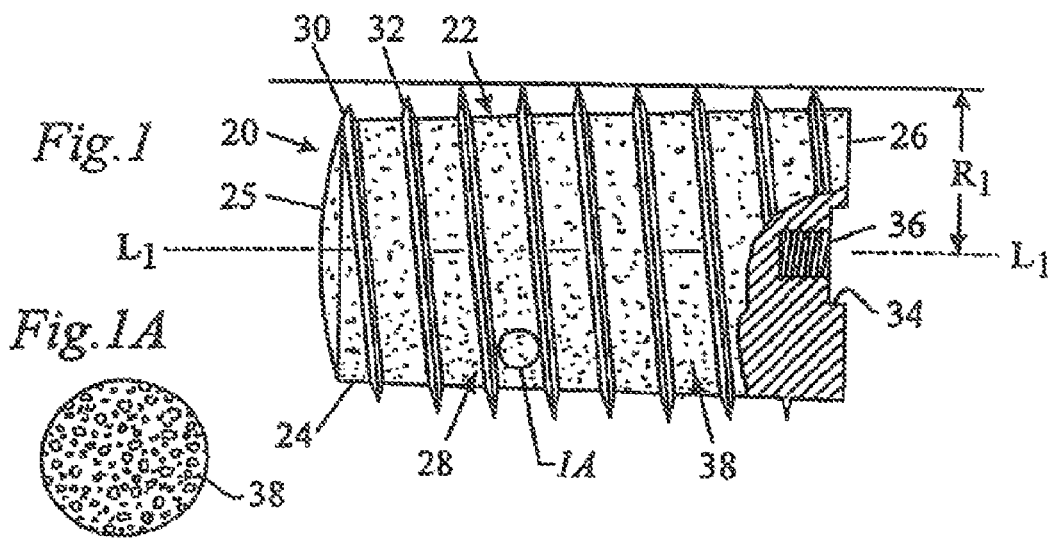
Fig.1
Fig.1A
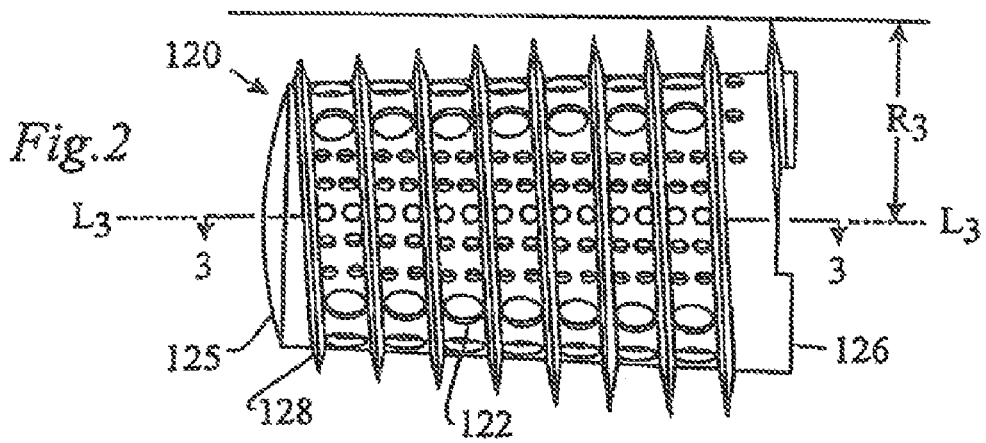
Fig.2
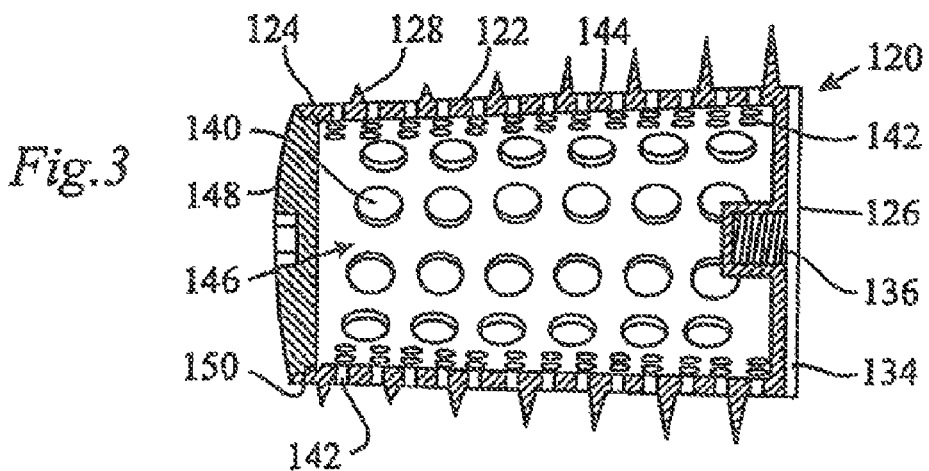
Fig.3

THREADED INTERBODY SPINAL FUSION IMPLANT

The present application is a continuation of application Ser. No. 12/454,393, filed May 18, 2009, now U.S. Pat. No. 7,828,800; which is a continuation of application Ser. No. 08/480,908, filed Jun. 7, 1995, now U.S. Pat. No. 7,534,254; which is incorporated herein by reference.

BACKGROUND OF THE INVENTION

1. Field of the Invention

The present invention relates generally to interbody spinal fusion implants, and in particular to spinal fusion implants configured to restore and maintain two adjacent vertebrae of the spine in anatomical lordosis.

2. Description of the Prior Art

Interbody spinal fusion refers to the method of achieving bony bridging between adjacent vertebrae through the disc space, the space between adjacent vertebrae normally occupied by a spinal disc. Numerous implants to facilitate such a fusion have been described by Cloward, Brantigan, and others, and are known to those skilled in the art. Generally, cylindrical implants offer the advantage of conforming to an easily prepared recipient bore spanning the disc space and penetrating into each of the adjacent vertebrae. Such a bore may be created by use of a drill. It is an anatomical fact that both the cervical spine and the lumbar spine are normally lordotic, that is convex forward. Such alignment is important to the proper functioning of the spine. Commonly, those conditions which require treatment by spinal fusion are associated with a loss of lordosis.

Therefore, there exists a need for spinal fusion implants that permit for the restoration of anatomical lordosis.

SUMMARY OF THE INVENTION

The present invention is directed to a variety of interbody spinal fusion implants having at least a partially frusto-conical configuration. In the preferred embodiment, the spinal fusion implants of the present invention have a body that is partially or fully frusto-conical shape substantially along the portion of the implant in contact with the adjacent vertebrae of the spine. The spinal fusion implants of the present invention have an external thread for engaging the adjacent vertebrae of the spine and have an insertion end and a trailing end. The external thread may have a variable or constant thread radius and/or a constant or variable thread height measured from the body of the implant.

The spinal fusion implants of the present invention may be further modified so that while the upper and lower surfaces are portions of a frusto-cone, at least one side portion may be truncated to form a planar surface that is parallel to the central longitudinal axis of the implant to form straight walls. These implants may have a more tapered aspect at the insertion end of the implant to facilitate insertion. The spinal fusion implants of the present invention may be relatively solid and/or porous and/or hollow, and may have surface roughenings to promote bone ingrowth and stability.

The spinal fusion implants of the present invention may have wells extending into the material of the implant from the surface for the purpose of holding fusion promoting materials and to provide for areas of bone ingrowth fixation. These wells, or holes, may pass either into or through the implant and may or may not intersect. The spinal fusion implants of the present invention may have at least one chamber which may be in communication through at least one opening to the surface of the implant. Said chamber may have at least one access opening for loading the chamber with fusion promoting substances. The access opening may be capable of being closed with a cap or similar means.

The spinal fusion implants of the present invention offer significant advantages over the prior art implants:

1. Because the spinal fusion implants of the present invention are at least partially frusto-conical in shape, those that taper from the leading edge to the trailing edge are easy to introduce and easy to fully insert into the spinal segment to be fused. In another embodiment, where the trailing edge of the implant is larger than the leading edge, the implant utilizes a tapered forward portion and an increasing thread height relative to the body from the leading edge to the trailing edge to facilitate insertion.
2. The shape of the implants of the present invention is consistent with the shape of the disc, which the implants at least in part replace, wherein the front of the disc is normally taller than the back of the disc, which allows for normal lordosis. The implants of the present invention are similarly taller anteriorly than they are posteriorly.
3. The spinal fusion implants of the present invention conform to a geometric shape, which shape is readily producible at the site of fusion, to receive said spinal fusion implants.

The spinal fusion implants of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bioabsorbable, and various ceramics or combination sufficient for the intended purpose. Further, the spinal fusion implants of the present invention may be made of a solid material, a mesh-like material, a porous material and may comprise, wholly or in part, materials capable of directly participating in the spinal fusion process, or be loaded with, composed of, treated of coated with chemical substances such as bone, morphogenic proteins, hydroxyapatite in any of its forms, and osteogenic proteins, to make them bioactive for the purpose of stimulating spinal fusion. The implants of the present invention may be wholly or in part bioabsorbable.

OBJECTS OF THE PRESENT INVENTION

It is an object of the present invention to provide a spinal fusion implant that is easily inserted into the spine, having a tapered leading end;

It is another object of the present invention to provide a spinal fusion implant that tapers in height from one end to the other consistent with the taper of a normal spinal disc;

It is yet another object of the present invention to provide a spinal fusion implant that is capable of maintaining anatomic alignment and lordosis of two adjacent vertebrae during the spinal fusion process;

It is still another object of the present invention to provide a spinal fusion implant that is self stabilizing within the spine;

It is yet another object of the present invention to provide a spinal fusion implant that is capable of providing stability between adjacent vertebrae when inserted;

It is still another object of the present invention to provide a spinal fusion implant that is capable of participating in the fusion process by containing, being composed of, or being treated with fusion promoting substances;

It is further another object of the present invention to provide a spinal fusion implant that is capable of spacing apart and supporting adjacent vertebrae during the spinal fusion process;

It is still further another object of the present invention to provide a spinal fusion implant that is consistent in use with the preservation of a uniform thickness of the subchondral vertebral bone;

It is another object of the present invention to provide a spinal fusion implant having a shape which conforms to an easily produced complementary bore at the fusion site; and It is a further object of the present invention to provide a frusto-conical spinal fusion implant which may be placed side by side adjacent to a second identical implant across the same disc space, such that the combined width of the two implants is less than sum of the individual heights of each implant.

It is a further object of the present invention to provide a frusto-conical spinal fusion implant which may be placed side by side adjacent to a second identical implant across the same disc space, such that the combined width of the two implants is less than sum of the individual lengths of each implant.

These and other objects of the present invention will become apparent from a review of the accompanying drawings and the detailed description of the drawings.

BRIEF DESCRIPTION OF THE DRAWINGS

FIG. 1 is a side elevational view of the spinal fusion implant of the present invention having a body that is frusto-conical with an external thread having a substantially uniform radius.

FIG. 1A is an enlarged fragmentary view along line 1A of FIG. 1 illustrating the surface configuration of the implant of FIG. 1.

FIG. 2 is an alternative embodiment of the spinal fusion implant of the present invention having a frusto-conical body with an external thread radius and thread height that are not constant.

FIG. 3 is as cross sectional view along line 3-3 of the implant of FIG. 2.

DETAILED DESCRIPTION OF THE PREFERRED EMBODIMENT

Figure 1B:
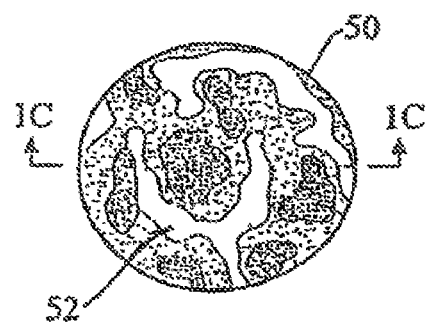
FIG. 1B is an enlarged fragmentary view along line 1A of FIG. 1 illustrating an alternative embodiment of the surface configuration of the implant of the present invention made of a cancellous material.
Figure 1C:
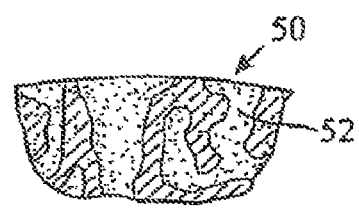
FIG. 1C is a cross sectional view along lines 1C-1C of FIG. 1B illustrating the alternative embodiment of the surface configuration of the implant of the present invention made of a cancellous material.

Referring to FIG. 1, a side elevational view of the spinal fusion implant of the present invention generally referred to by numeral 20 is shown. The implant 20 has a body 22 that is frusto-conical in shape such that the body 22 has a diameter (root diameter) that is generally frusto-conical. The body 22 has an insertion end 24 and a trailing end 26. The insertion end 24 may include a tapered portion 25 to facilitate insertion of the spinal implant 20. In the preferred embodiment, when the implant 20 is inserted from the anterior aspect of the spine, the body 22 of the implant 20 has a maximum diameter at a point nearest to the trailing end 26 and a minimum diameter at a point nearest to the insertion end 24.

The implant 20 has an external thread 28 having a substantially uniform radius $R_1$ measured from the central longitudinal axis $L_1$ of the implant 20. The outer locus of the external thread 28 (major diameter) has an overall configuration that is substantially parallel to the longitudinal axis $L_1$. While the major diameter of the implant 20 is substantially uniform, the external thread 28 may be modified at the leading edge by having initially a reduced thread radius to facilitate insertion of the implant 20 and may also be modified to make the external thread 28 self-tapping. In the preferred embodiment, the external thread 28 has a first thread 30 of a lesser radius than the radius $R_1$ of the remainder of the external thread 28 to facilitate insertion of the implant 20. The second thread 32 has a greater radius than the first thread 30, but is still shorter than the radius $R_1$ of the remainder of the external thread 28 which is thereafter of constant radius.

The body 22 is frusto-conical substantially along the portion of the body 22 in contact with the adjacent vertebrae of the spine which allows for creating and maintaining the adjacent vertebrae of the spine in the appropriate angular relationship to each other in order to preserve and/or restore the normal anatomic lordosis of the spine. The substantially uniform radius $R_1$ of the external thread 28 of the implant 20 allows engaging the bone of the adjacent vertebrae in a position that counters the forces which tend to urge the implant 20 from between the adjacent vertebrae in the direction opposite to which the implant 20 was implanted. The greater thread height measured from the body 22 near the leading end 24 of the implant 20 provides greater purchase into the vertebral bone and again enhances the stability of the implant 20. Further, the configuration of the external thread 28 increases the surface area of the implant 20 in contact with the vertebrae to promote bone ingrowth.

The implant 20 has a recessed slot 34 at its trailing end 26 for receiving and engaging insertion instrumentation for inserting the implant 20. The recessed slot 34 has a threaded opening 36 for threadably attaching the implant 20 to instrumentation used for inserting the implant 20.

Referring to FIG. 1A, the implant 20 has an outer surface 38 that is porous to present an irregular surface to the bone to promote bone ingrowth. The outer surface 38 is also able to hold fusion promoting materials and provides for an increased surface area to engage the bone in the fusion process and to provide further stability. The pores of the outer surfaces 38 are microscopic in size having a diameter that is less than 1 mm, in the range of 50-1000 microns, with 250-500 microns being the preferred diameter. It is appreciated that the outer surface 38, and/or the entire implant 20, may comprise any other porous material or roughened surface sufficient to hold fusion promoting substances and/or allow for bone ingrowth and/or engage the bone during the fusion process. The implant 20 may be further coated with bioactive fusion promoting substances including, but not limited to, hydroxyapatite compounds, osteogenic proteins and bone morphogenic proteins. The implant 20 is shown as being solid, however it is appreciated that it can be made to be substantially hollow or hollow in part.

Referring to FIG. 1B, an enlarged fragmentary view along line 1A of FIG. 1 illustrating an alternative embodiment of the surface configuration 38 of the implant of the present invention made of a cancellous material is shown. The cancellous material 50, similar in configuration to human cancellous bone, having interstices 52 such that the outer surface 38 has a configuration as shown in FIGS. 1B and 1C. As the implant of the present invention may be made entirely or in part of the cancellous material 50, the interstices 52 may be present in the outer surface 338 and/or within the entire implant to promote bone ingrowth and hold bone fusion promoting materials.

Figure 1D:
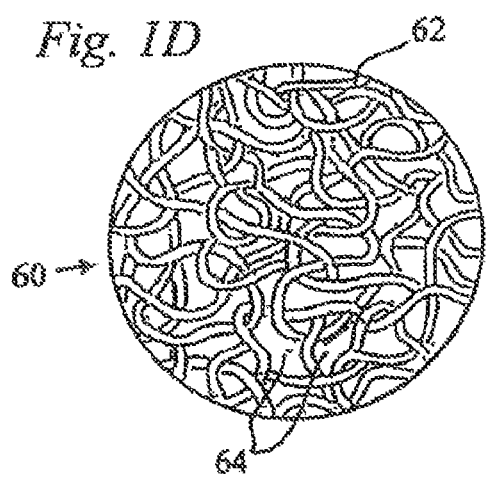
FIG. 1D is an enlarged fragmentary view along line 1A of FIG. 1 illustrating an alternative embodiment of the surface configuration of the implant of the present invention made of a fibrous mesh-like material.

Referring to FIG. 1D, an enlarged fragmentary view along line 1A of FIG. 1 illustrating an alternative embodiment of the surface configuration of the implant of the present invention made of a fibrous mesh-like material is shown. The mesh-like material 60 comprises strands 62 that are formed and pressed together such that interstices 64, capable of retaining fusion promoting material and for allowing for bone ingrowth, are present between the strands in at least the outer surface 38 of implant of the present invention.

Figure 1E:
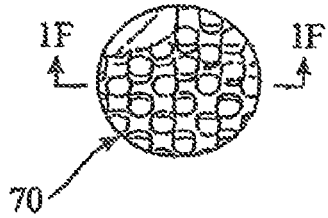
FIG. 1E is a fragmentary view along line 1A of FIG. 1 illustrating an alternative embodiment of the surface configuration, of the implant of the present invention comprising a plurality of spaced apart posts.
Figure 1F:
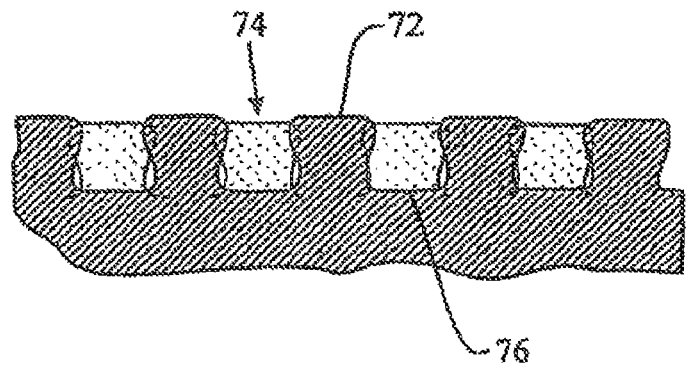
FIG. 1F is an enlarged fragmentary sectional view along lines 1F-1F of FIG. 1E illustrating the surface configuration of the implant of FIG. 1E.

Referring to FIGS. 1E and 1F, a fragmentary view along line 1A of FIG. 1 illustrating an alternative embodiment of the surface configuration 38 of the implant of the present invention comprising a plurality of spaced apart posts 70 is shown. The posts 70 have a head portion 72 of a larger diameter than the remainder of the posts 70, and each of the interstices 74 is the reverse configuration of the posts 72, having a bottom 76 that is wider than the entrance to the interstices 74. Such a configuration of the posts 70 and interstices 74 aids in the retention of bone material in the surface 38 of the implant and further assists in the locking of the implant into the bone fusion mass created from the bone ingrowth. As the bone ingrowth at the bottom 76 of the interstices is wider than the entrance, the bone ingrowth cannot exit from the entrance and is locked within the interstice 74. The surface of the implant provides for an improvement in the available amount of surface area which may be still further increased by rough finishing, flocking or otherwise producing a non smooth surface.

In the preferred embodiment, the posts 70 have a maximum diameter in the range of approximately 0.1-2 mm and a height of approximately 0.1-2 mm and are spaced apart a distance of approximately 0.1-2 mm such that the interstices 74 have a width in the range of approximately 0.1 to 2 mm. The post sizes, shapes, and distributions may be varied within the same implant.

In the preferred embodiment, for use in the lumbar spine, the implant 20 has an overall length in the range of approximately 24 mm to 32 mm with 26 mm being the preferred length. The body 22 of the implant 20 has a root diameter at the insertion end 24 in the range of 8-20 mm, with 14-16 mm being the preferred root diameter at the insertion end, and a root diameter at the trailing end 26 in the range of 10-24 mm, with 16-18 mm being the preferred diameter at the trailing end 26, when said implants, are used in pairs. When used singly in the lumbar spine, the preferred diameters would be larger.

In the preferred embodiment, the implant 20 has a thread radius $R_1$ in the range of 6 mm to 12 mm, with 9-10 mm being the preferred radius $R_1$. For use in the cervical spine, the implant 20 has an overall length in the range of approximately 10-22 mm, with 12-14 mm being the preferred length. The body 22 of the implant 20 has a root diameter at the insertion end 24 in the range of 8-22 mm, with 16-18 mm being the preferred root diameter at the insertion end when used singly, and 8-10 mm when used in pairs. The body 22 of the implant 20 has a root diameter at the trailing end 26 in the range of 10-24 mm, with 18-20 mm being the preferred root diameter at the trailing end 26 when used singly, and 10-12 mm when used in pairs; a thread radius, $R_1$ in the range of approximately 4-12 mm, with 9-10 mm being the preferred radius $R_1$ when inserted singularly and 5-7 mm when inserted side by side in pairs.

Referring to FIG. 2, an alternative embodiment of implant 20 is shown and generally referred to by the numeral 120. The implant 120 has a body 122 similar to body 122 of implant 120 and has an external thread 128 having a radius $R_3$ measured from the central longitudinal axis $L_3$ of the implant 120. The thread radius $R_3$ is not constant throughout the length of the implant 120 and the external thread 128 has a thread height that is also not constant with respect to the body 122 of the implant 120. In the preferred embodiment, the implant 120 has an external thread 128 with a radius $R_3$ that increases in size from the insertion end 124 to the trailing end 126 of the implant 120.

Referring to FIG. 3, a cross sectional view along line 3-3 of the implant 120 is shown. The implant 120 has an outer wall 144 surrounding an internal chamber 146. The large and small openings 140 and 142 may pass through the outer wall 144 to communicate with the internal chamber 146. The internal chamber 146 may be filled with bone material or any natural bone growth material or fusion promoting material such that bone growth occurs from the vertebrae through the openings 140 and 142 to the material within internal chamber 146. While the openings 140 and 142 have been shown in the drawings as being circular, it is appreciated that the openings 140 and 142 may have any shape, size configuration or distribution, suitable for use in a spinal fusion implant without departing from the scope of the present invention.

The openings 140 and 142 are macroscopic in size having a diameter that is greater than 1 mm. The large openings 140 have a diameter in the range of 206 mm, with the preferred diameter being 3.5 mm; and the small openings have a diameter in the range of 1-2 mm, with 1.5 mm being the preferred diameter.

The implant 120 has a cap 148 with a thread 150 that threadably attaches to the insertion end 124 of the spinal fusion implant 120. The cap 148 is removable to provide access to the internal chamber 146, such that the internal chamber 146 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 148 and/or the spinal fusion implant 120 may be made of any material appropriate for human implantation including metals such as cobalt chrome, stainless steel, titanium, plastics, ceramics, composites and/or may be made of, and/or filled, and/or coated with a bone ingrowth inducing material such as, but not limited to, hydroxyapatite or hydroxyapatite tricalcium phosphate or any other osteoconductive, osteoinductive, osteogenic, or other fusion enhancing material. The cap 148 and the implant 120 may be partially or wholly bioabsorbable.

Figure 4:
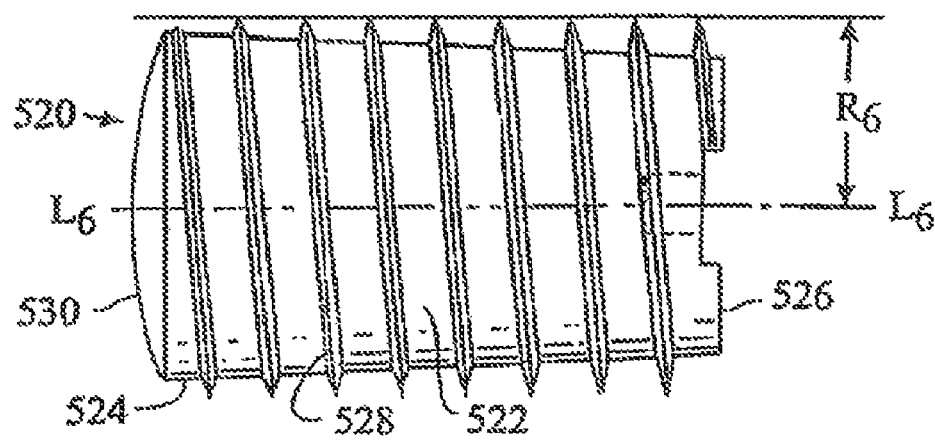
FIG. 4 is a side elevational view of an alternative embodiment of the spinal fusion implant of the present invention.

Referring to FIG. 4, a side elevational view of an alternative embodiment of the spinal fusion implant of the present invention generally referred to by numeral 520 is shown. The implant 520 has a body 522 having a root diameter that is frusto conical in the reverse direction as that implant 20 shown in FIG. 1, in order to preserve and/or restore lordosis in a segment of spinal column when inserted from the posterior aspect of the spine. The body 522 has an insertion end 524 and a trailing end 526. In the preferred embodiment, the body 522 of the implant 520 has a minimum diameter at a point nearest to the trailing end 526 and a maximum diameter at a point nearest to the insertion end 524. The insertion end 524 may have an anterior nose cone portion 530 presenting a tapered end to facilitate insertion.

The implant 520 has an external thread 528 having a substantially uniform radius $R_6$ measured from the central longitudinal axis $L_6$ of the implant 520 such that the external diameter of the external thread 528 (major diameter) has an overall configuration that is substantially parallel to the longitudinal axis $L_6$. It is appreciated that the thread 528 can have a major diameter that varies with respect to the longitudinal axis $L_6$, such that the major diameter may increase from the insertion end 524 to the trailing end 526 or the reverse. The external thread 528 has a thread height measured from the body 522 that increases from the insertion end 524 to the trailing end 526.

Figure 5:
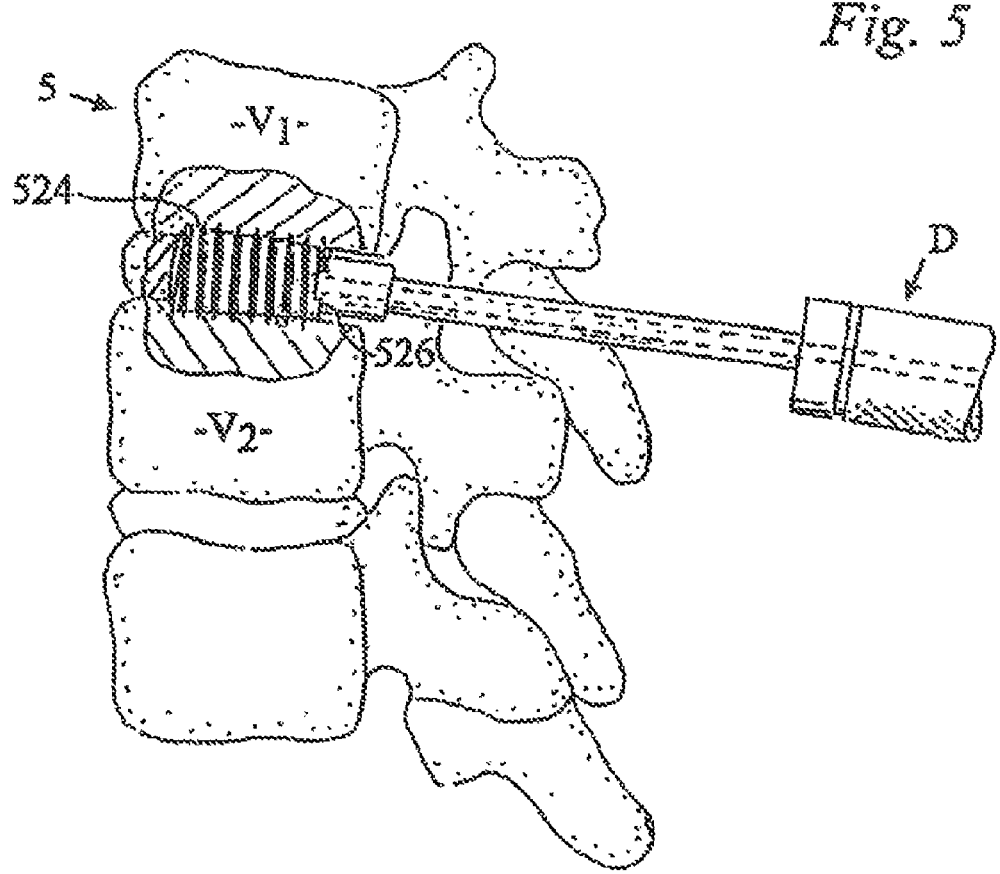
FIG. 5 is a side elevational view and partial cut-away of a segment of the spinal column in lordosis showing the spinal fusion implant of FIG. 4 being implanted with a driving instrument from the posterior approach to the spinal column.

Referring to FIG. 5, a segment of the spinal column S is shown with the vertebrae $V_1$ and $V_2$ in lordosis and an implant 520 shown being inserted from the posterior aspect of the spinal column S with an instrument driver D. The implant 520 is inserted with the larger diameter insertion end 524 first in order to in initially distract apart the vertebrae $V_1$ and $V_2$ which then angle toward each other posteriorly as the implant 520 is fully inserted. It is appreciated that the insertion of implant 520 does not require the adjacent vertebrae $V_1$ and $V_2$ to be placed in lordosis prior to insertion, as the full insertion of the implant 520 itself is capable of creating the desired lordotic angular relationship of the two vertebrae $V_1$ and $V_2$.

In the preferred embodiment, for use in the lumbar spine, the implant 520 has an overall length in the range of approximately 24 m 30 mm, with 26 mm being the preferred length. The body 522 of the implant 520 has a root diameter at the insertion end 524 in the range of 12-22 mm, with 16 mm being the preferred root diameter at the-insertion end, and a root diameter at the trailing end 526 in the range of 10-20 mm, with 14 mm being the preferred diameter at the trailing end 526. In the preferred embodiment, the implant 520 has a thread radius $R_6$ in the range of 6 mm to 12 mm, with 8 mm being the preferred radius $R_6$.

Figure 6:
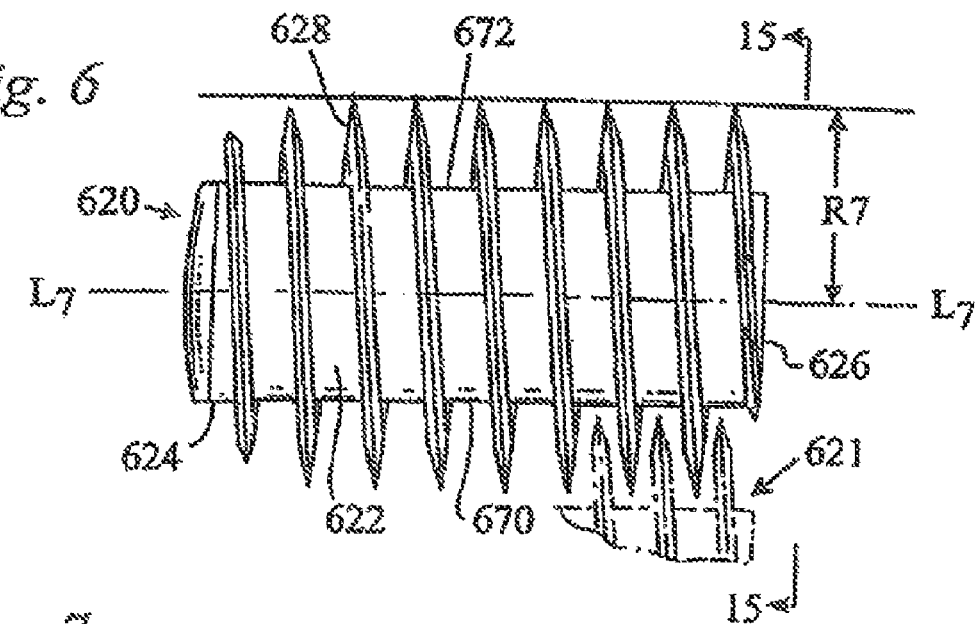
FIG. 6 is a side elevational view of an alternative embodiment of the spinal fusion implant of the present invention having a frusto-conical body and truncated sides.

Referring to FIG. 6, an alternative embodiment of the spinal fusion implant of the present invention generally referred to by the numeral 620 and a partial fragmentary view of a second identical implant, generally referred to by the numeral 621 are shown. The implant 620 has a body 622 that is partially frusto-conical in shape similar to body 22 of implant 20 shown in FIG. 1, and has an insertion end 624 and a trailing end 626. The body 622 of the implant 620 has truncated sides 670 and 672 forming planar surfaces that are parallel to the longitudinal axis $L_7$. In this manner, two implants 620 and 621 may be placed side by side, with one of the sides 670 or 672 of each implant with little space between them, such that the area of contact with the bone of the adjacent vertebrae is maximized. It is appreciated that the body 622 may also be cylindrical in shape and have truncated sides 670 and 672.

The implant 620 has an external thread 628 having a radius $R_6$ measured from the central longitudinal axis $L_7$ that may be constant, such that the major diameter or outer locus-of the external thread 628 has an overall configuration that is substantially, cylindrical. It is appreciated that the external thread 628 may have a thread radius $R_7$ that is variable with respect to the longitudinal axis $L_7$ such that the major diameter or outer locus of the external thread 628 has an overall configuration that is substantially frusto-conical.

Figure 7:
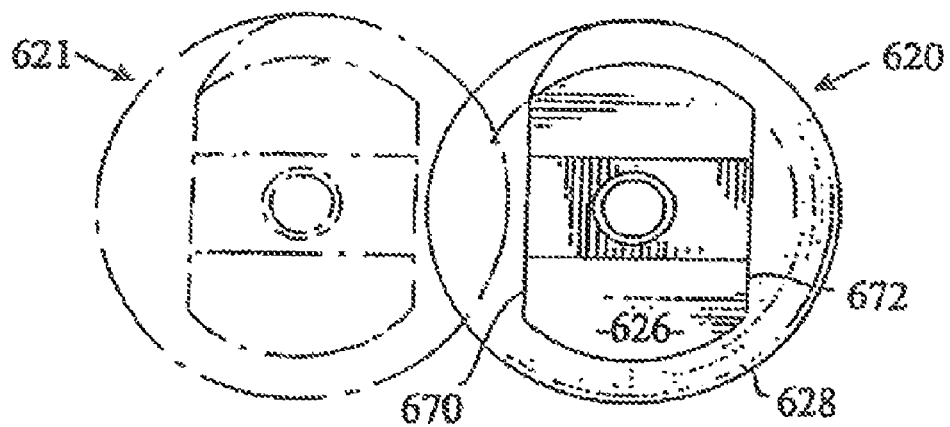
FIG. 7 is an end view along line 7-7 of the spinal fusion implant of FIG. 6 shown placed beside a second identical implant shown in hidden line.

Referring to FIG. 7, an end view of the implant 620 placed beside implant 621 is shown. The implant 620 has a thread radius that is substantially constant and has a thread height measured from the body 622 that is greater at the sides 670 and 672. In this manner, two implants 620 and 621 can be placed beside each other with the external thread 628 of each implant interdigitated allowing for closer adjacent placement of the two implants as a result of the substantial overlap of the external thread 628 at the side 670 or 672 of the implants.

Figure 8:
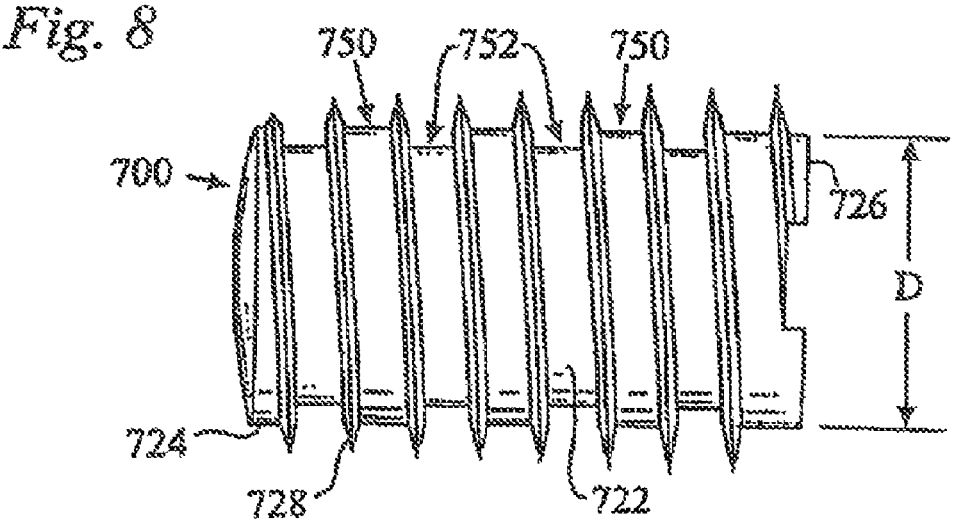
FIG. 8 is a side elevational view of an alternative embodiment of the spinal fusion implant of the present invention having a body with an irregular configuration.

Referring to FIG. 8, an alternative embodiment of the implant of the present invention is shown and generally referred to by the numeral 700. The implant 700 is similar in configuration to implant 20 shown in FIG. 1, except that the body 722 has an irregular configuration. The configuration of the body 722 has a root diameter D which is variable in size throughout the length of the implant 700 and, as shown in this embodiment, comprises larger diameter portions 750 and smaller diameter portions 752. It is appreciated that each of the large diameter portions 750 may be of the same or different diameter and each of the smaller diameter portions 752 may be of the same or different diameter.

The outer surface of the body 722 of implant 720 may be filled with fusion promoting substances such that the smaller diameter portions 752 may hold such fusion promoting substances. If so filled, the composite of the implant 700 and the fusion promoting material could still produce an even external surface of the body 722 if so desired.

While the present invention has been described in detail with regards to the preferred embodiments, it is appreciated that other variations of the present invention may be devised which do not depart from the inventive concept of the present invention. In particular, it is appreciated that the various teachings described in regards to the specific embodiments herein may be combined in a variety of ways such that the features are not limited to the specific embodiments described above.

Each of the features disclosed in the various embodiments and their functional equivalents may be combined in any combination sufficient to achieve the purposes of the present invention as described herein.

I claim:

1. An interbody spinal fusion implant for insertion within an implantation space formed across the height of a disc space between adjacent vertebral bodies of a human spine, said implant comprising:
   a body having a leading end for insertion first into the disc space, a trailing end opposite said leading end, a mid-longitudinal axis through said leading and trailing ends, and opposed arcuate portions between said leading and trailing ends adapted to be placed within the implantation space oriented toward the adjacent vertebral bodies, respectively, one of said opposed arcuate portions adapted to contact one of said adjacent vertebral bodies, and the other of said opposed arcuate portions adapted to contact the other said adjacent vertebral bodies, said opposed arcuate portions maintaining a spaced relationship between the adjacent vertebral bodies in the implantation space; and
   a thread extending from at least adjacent said leading end to at least adjacent said trailing end, said thread adapted to engage said implant to the adjacent vertebral bodies and to facilitate rotation of said implant from a first position to a second position during insertion thereof into the implantation space, said body having a plurality of openings between one complete turn of said thread, each of said openings having a maximum cross sectional dimension, the maximum cross sectional dimension of at least two of said openings being different, at least two of said openings being in communication with one another to permit for the growth of bone from adjacent vertebral body to adjacent vertebral body through said implant.

2. The implant of claim 1, wherein the maximum cross sectional dimension of one of said openings is more than twice the maximum cross sectional dimension of another of said openings.

3. The implant of claim 1, wherein the maximum cross sectional dimension of one of said openings is generally the same as the distance between two adjacent turns of said thread.

4. The implant of claim 1, wherein said body includes a length parallel to the mid-longitudinal axis, at least two of said openings being positioned adjacent one another along the length of said implant and between two adjacent turns of said thread.

5. The implant of claim 4, wherein said adjacent openings each have a diameter, the diameter of said adjacent openings being the same.

6. The implant of claim 4, wherein said adjacent openings form a pair of openings, further comprising a plurality of said pairs of openings between said two adjacent turns of said thread.

7. The implant of claim 4, wherein each of said plurality of openings has a central longitudinal axis, said plurality of openings including at least two larger openings each having a maximum cross sectional dimension larger than the cross sectional dimension of each of said adjacent openings, the central longitudinal axes of said two larger openings forming a line therethrough bisecting the distance between the central longitudinal axes of said adjacent openings.

8. The implant of claim 1, wherein said body has an internal chamber capable of containing fusion promoting material.

9. The implant of claim 1, wherein said thread has a variable height along each turn of said thread about the mid-longitudinal axis of said body.

10. The implant of claim 1, wherein said thread is uninterrupted.

11. The implant of claim 1, wherein an outer locus of said thread has a substantially cylindrical configuration.

12. The implant of claim 1, wherein said body has a substantially cylindrical configuration.

13. The implant of claim 1, wherein said implant is at least in part bioabsorbable.

14. The implant of claim 1, in combination with a fusion promoting substance.

15. An interbody spinal fusion implant for insertion within an implantation space formed across the height of a disc space between adjacent vertebral bodies of a human spine, said implant comprising:

a body having a leading end for insertion first into the disc space, a trailing end opposite said leading end, a mid-longitudinal axis through said leading and trailing ends, and opposed arcuate portions between said leading and trailing ends adapted to be placed within the implantation space oriented toward the adjacent vertebral bodies, respectively, one of said opposed arcuate portions adapted to contact one of said adjacent vertebral bodies, and the other of said opposed arcuate portions adapted to contact the other said adjacent vertebral bodies, said opposed arcuate portions maintaining a spaced relationship between the adjacent vertebral bodies in the implantation space; and a thread extending from at least adjacent said leading end to at least adjacent said trailing end, said thread adapted to engage said implant to the adjacent vertebral bodies and to facilitate rotation of said implant from a first position to a second position during insertion thereof into the implantation space, said body having a plurality of openings being along a helical path between turns of said thread and around the mid-longitudinal axis, each of said openings having a maximum cross sectional dimension, the maximum cross sectional dimension of at least two of said openings being different along said helical path, at least two of said openings being in communication with one another to permit for the growth of bone from adjacent vertebral body to adjacent vertebral body through said implant.

16. The implant of claim 15, wherein the maximum cross sectional dimension of one of said openings is more than twice the maximum cross sectional dimension of another of said openings.

17. The implant of claim 15, wherein the maximum cross sectional dimension of one of said openings is generally the same as the distance between two adjacent turns of said thread.

18. The implant of claim 15, wherein said body includes a length parallel to the mid-longitudinal axis, at least two of said openings being positioned adjacent one another along the length of said implant and between two adjacent turns of said thread.

19. The implant of claim 18, wherein said adjacent openings each have a diameter, the diameter of said adjacent openings being the same.

20. The implant of claim 18, wherein said adjacent openings form a pair of openings, further comprising a plurality of said pairs of openings between said two adjacent turns of said thread.

21. The implant of claim 18, wherein each of said plurality of openings has a central longitudinal axis, said plurality of openings including at least two larger openings each having a maximum cross sectional dimension larger than the cross sectional dimension of each of said adjacent openings, the central longitudinal axes of said two larger openings being along a line therethrough bisecting the distance between the central longitudinal axes of said adjacent openings.

22. The implant of claim 15, wherein said body has an internal chamber capable of containing fusion promoting material.

23. The implant of claim 15, wherein said thread has a variable height along each turn of said thread about the mid-longitudinal axis of said body.

24. The implant of claim 15, wherein said thread is uninterrupted.

25. The implant of claim 15, wherein an outer locus of said thread has a substantially cylindrical configuration.

26. The implant of claim 15, wherein said body has a substantially cylindrical configuration.

27. The implant of claim 15, wherein said implant is at least in part bioabsorbable.

28. The implant of claim 15, in combination with a fusion promoting substance.

* * * * *

UNITED STATES PATENT AND TRADEMARK OFFICE
CERTIFICATE OF CORRECTION

PATENT NO.           : 8,057,475 B2                                    Page 1 of 1
APPLICATION NO.      : 12/942671
DATED                : November 15, 2011
INVENTOR(S)          : Gary Karlin Michelson It is certified that error appears in the above-identified patent and that said Letters Patent is hereby corrected as shown below:

Title Page 1, item (56), References Cited:
U.S. Patent Documents, line 5 thereof: change "Moreira" to -- De G. Moreira --.

Title Page 2, item (56), Column 1:
Line 9: change "3,848,001" to -- 8,848,601 --.

Title Page 3, item (56), Column 2:
Line 18: change "Brit. Surg ," to -- Brit. J. Surg., --;
Line 26: change "Sincipitai" to -- Sincipital --; and change "Sung.," to -- Surg., --;
Line 30: change "n. Horses" to -- in Horses --;
Line 37: change "Turnorresektionen" to -- Tumorresektionen --;
Line 47: change "Interbody" to -- interbody --;
Line 48: change "61793-794" to -- 61:793-794 --; and
Line 53: change "Maxtilofac" to -- Maxillofac --.

Title Page 4, item (56), Column 2:
Line 9: change "Principies" to -- Principles --; and
Line 30: change "J,B," to -- J.B. --.

Signed and Sealed this
Twenty-first Day of February, 2012

David J. Kappos
*Director of the United States Patent and Trademark Office*